United States Patent
Chou

[11] Patent Number: 5,945,592
[45] Date of Patent: Aug. 31, 1999

[54] SYSTEM AND METHOD FOR ISOTOPE RATIO ANALYSIS AND GAS DETECTION BY PHOTOACOUSTICS

[75] Inventor: Mau-Song Chou, Rancho Palos Verdes, Calif.

[73] Assignee: TRW Inc., Redondo Beach, Calif.

[21] Appl. No.: 09/162,682

[22] Filed: Sep. 29, 1998

Related U.S. Application Data

[62] Division of application No. 08/592,748, Aug. 3, 1995.

[51] Int. Cl.$^6$ .................................................. G01N 29/02
[52] U.S. Cl. ........................................ 73/24.01; 73/24.02
[58] Field of Search ............................... 73/24.02, 24.01, 73/31.01, 31.02, 31.03

[56] References Cited

U.S. PATENT DOCUMENTS

| | | | |
|---|---|---|---|
| Re. 33,493 | 12/1990 | Lee et al. ................................. | 250/343 |
| 4,516,858 | 5/1985 | Gelbwachs ............................... | 356/437 |
| 4,684,805 | 8/1987 | Lee et al. ................................. | 250/343 |
| 5,284,054 | 2/1994 | Loebach ................................... | 73/23.3 |
| 5,394,236 | 2/1995 | Murnick ................................... | 356/311 |

OTHER PUBLICATIONS

West et al., "Photoacoustic Spectroscopy", Rev. Sci. Instrum., vol. 54, No. 07, Jul. 1983, pp. 797–817.

*Primary Examiner*—Daniel S. Larkin
*Attorney, Agent, or Firm*—Michael S. Yatsko

[57] ABSTRACT

The system and method are set forth for photoacoustical analysis of isotope and other compounds having telltale absorption wavelenghths between 1700–2500 nm. The system and method includes a Co:Mg $F_2$, optical parametric oscillator (OPO) or diode laser tunable between 1700–2500 nm which is directed into a sample at energies sufficient to generate detectable acoustical emissions. A microphone detects the emissions for processing and analysis. The system and method is adapted to detect stable isotope compounds such as $^{13}CO_2$ as well as other chemical compounds. For non-gaseous compounds, a $CO_2$ or diode laser is used to photoablate the gaseous sample containing the suspected compound.

10 Claims, 4 Drawing Sheets

SYSTEM AND METHOD FOR ISOTOPE RATIO ANALYSIS AND GAS DETECTION BY PHOTOACOUSTICS

CROSS-REFERENCE TO RELATED APPLICATIONS

This application is a divisional application of application Ser. No. 08/592,748 filed Aug. 3, 1995.

This invention was made with federal government support under Contract No. F04611-87-C-0087. The federal government, therefore, has certain rights to the invention.

BACKGROUND

This invention relates to systems and methods for isotope ratio analysis and gas detection, and more particularly to systems and methods for isotope ratio analysis and gas detection using photoacoustics.

In the medical field it has been known to use radioactive isotope labeled compounds to study various conditions. However, the use of radioactive isotopes creates a problem not only from a storage and disposal standpoint, but also from the standpoint that the dosage provided to the patient must be monitored to avoid excessive radiation, illness or other discomfort.

To depart from the drawbacks associated with the use radioactive isotopes, it has been known that a variety of medical conditions can be examined using stable, non-radioactive isotopes. As described in Lee, U.S. Pat. No. 4,684,805, the metabolism of fat can be examined by monitoring the subject's breath after administration of a stable, non-radioactive isotope-labeled fat. Specifically, $^{13}$C-labeled fat can be administered to the subject, the fat being metabolized and the isotope eliminated from the subject as $^3CO_2$ during exhalation. The presence and/or concentration of the $^{13}CO_2$ or the ratio of its concentration to naturally occurring $^{12}CO_2$ can be used to analyze the metabolism and its rate under study.

Similarly ileal and liver disfunction can be examined by monitoring exhaled breath following injections of $^{13}$C-labeled bile acid and galactose and examining the exhaled breath for the $^{13}$C isotope present as $^{13}CO_2$. Small intestine bacterial overgrowth can be examined by monitoring exhaled breath for the labeling isotope again occurring as $^{13}CO_2$ following intake of $^{13}$C labeled xylose.

Marshall, U.S. Pat. No. 4,830,010 discloses the use of isotope-labeled urea for diagnosis of gastrointestinal disorders.

As can be appreciated, where applicable, the use of a stable, non-radioactive isotope has vast advantages over the use of a radioactive isotope not only from the storage and disposal standpoint associated with the use of radioactive isotopes but also from a health standpoint.

The shift from use of radioactive isotopes to stable, non-radioactive isotopes in medical analysis only has significant utility if there are satisfactory means and techniques to detect the presence of a labeling isotope. Mass spectrometry is often used for chemical analysis of stable isotopes. A drawback with this technique, however, is that it requires a very high quality vacuum, elaborate sample preparation to remove low levels of water vapor and/or is relatively expensive from an equipment and technician labor standpoint. Furthermore, the mass spectrometric method cannot readily differentiate between compounds with the same mass: for example, $^{13}CO_2$ from $^{12}COOH$ and $^{12}C^{16}O^{17}O$.

Accordingly, if the use of stable, non-radioactive isotopes to study, for example, metabolic rate in a patient are to gain popularity and replace some tests heretofore requiring radioactive isotopes, there is a fundamental need for methods and devices to detect the presence of the labeling, stable, non-radioactive isotope which overcomes the problems associated with the analysis techniques identified above.

In addition to the medical field, isotopic study can also be useful in the geological field. Analysis of the ratio of $^{13}CO_2$ to $^{12}CO_2$ in sedimentation of carbonates or in the atmosphere is important to determine the cycle of $CO_2$ production and absorption. In Crandall, U.S. Pat. No. 4,517,461 geochemical oil exploration and prospecting by measurement of isotopic compositions of large numbers of individual organic compounds of oil samples is described, to be used to predict locations of other oil reserves or where the oil may have migrated from a common source or formation. In this system there is a need for a detector to detect the presence of the isotope compounds or constituents of interest, which does not suffer from the problems and drawbacks of the analysis techniques such as mass spectroscopy described above.

Still further and as a departure from isotopic analysis, there is a general need for a detector to detect the presence of certain other suspected constituents in a sample. As but several examples, air samples can be monitored and analyzed for toxic vapors such as CO, $NH_3$, HCl, $H_2S$ and HF in or about a chemical plant or a power plant or the like. Fast, reliable, and economic detectors directed to the presence of such constituents would constitute a valuable tool to combat pollution and to detect the escape, discharge or presence of harmful compounds. Many current chemical analysis techniques are often unsatisfactory in that they are slow and expensive.

On-Road vehicle emission inspections for pollutants is also important to intercept major pollution offenders and to improve overall air quality. Again, a fast, reliable and accurate method of detection and detector would be a valuable tool to combat air pollution.

As but other examples where a detector and method which is fast, economical and reliable would be important would be in sampling air proximate a natural gas pipeline to determine the presence of leaks. Soil samples which may contain certain dense nonaqueous phase layer chemicals (DNALP) such as chlorobenzene and others as a pollutant are also in need of a detection method, system and detector which is fast, economical and reliable to detect the presence of such pollutants.

As another example, in military or security fields, a fast, reliable and accurate detector and method is needed to determine the presence of explosives or chemical warfare compounds.

The foregoing are but several examples where there is a need for a reliable, inexpensive detector which does not suffer from the drawbacks of mass spectrometry or gas chromatography.

SUMMARY OF THE INVENTION

There is set forth according to the present invention a photoacoustic system and method for detecting a selected constituent in a gas, the constituent having at least one absorption wavelength in the range of approximately 1700 to 2500 nm. There is also set forth a system and method for examining a metabolic condition of an organism through the introduction of a stable isotope compound to the organism, the isotope liberated from the organism as a sample containing constituent molecules including the isotope having at least one absorption wavelength of between 1700 and 2500 nm, and photoacoustically analyzing the liberated sample from the organism to detect the subject isotope containing constituent. Determining the presence and concentration of the constituent can then be used to determine how the isotope containing compound is metabolized by the organism.

Still further there is set forth a system and method for using photoacoustic detection of a constituent contained in a non-gaseous sample, the constituent having an absorption wavelength of between approximately 1700 and 2500 nm.

Toward this end, there is set forth a photoacoustic system and method for detecting a selected constituent in a gas, the constituent having at least one telltale or fingerprint absorption wavelength in the range of about 1700 to 2500 nm. The system and method include a source of electromagnetic radiation tunable to selected wavelengths between 1700 to 2500 nm to correspond to the one or more fingerprint wavelengths of the suspected constituent. The radiation is directed into the sample to be absorbed by the constituent. Absorption of the electromagnetic radiation of wavelengths corresponding to the absorption wavelength excites the constituent molecules causing them to collide with surrounding molecules to generate detectable acoustical emissions. For this purpose the electromagnetic source has sufficient energy to generate acoustical emissions in the sample in response to absorption. It has been found that a pulsed $Co:MgF_2$ laser having an energy output of approximately 1 to 160 mJ per pulse induces relatively strong acoustic emissions for detection and measurement. A detector such as a microphone is used to detect the acoustic emissions and produce, in response, an electrical signal proportional to the acoustical emission. A data processor processes the electric signals to extract the detected acoustic emissions from background acoustical emissions and averages those emissions over a plurality of pulses of radiation thereby improving the signal to noise ratio.

In a specific application, a metabolic condition of an organism is examined using this photoacoustic detection system and method above. The method includes introducing a stable isotope compound into the organism for uptake by the metabolic system under study. The compound is metabolized by the organism and the isotope is passed from the organism as, for example, exhalation. For example, the stable isotope may be $^{13}C$ administered as a $^{13}C$-labeled fat, $^{13}C$-labeled bile acid and galactose, or $^{13}C$-labeled xylose which, when metabolized, is liberated by exhalation of the patient as $^{13}CO_2$. The output of a laser is directed into the exhalation sample, the laser tuned to wavelengths corresponding to the fingerprint absorption wavelengths of the $^{13}CO_2$ and having sufficient energy to generate acoustical emissions in response to the presence of the constituent isotope, i.e. $^{13}CO_2$. Again, it has been found that a pulsed $Co:MgF_2$ laser tunable between 1700 and 2500 nm and having an energy output of approximately 1 to 160 mJ per pulse is particularly adapted to detect the presence of stable isotope compounds such as $^{13}CO_2$ having the aforesaid fingerprint wavelengths within that range. The acoustical emissions generated as a result of absorbed energy are detected by a microphone and an electrical signal proportional to the acoustic emissions are generated and processed to extract the constituent gas acoustical emissions from any background acoustical emissions, and to average the emissions over a plurality of laser pulses to improve the signal to noise ratio. The concentration of $^{13}CO_2$ and/or the ratio of $^3CO_2$ to naturally occurring $^{12}CO_2$ can be analyzed over time to determine the rate the $^{13}C$-labelled fat or other labeled compound is metabolized. Analysis of the breath $CO_2$ may be carried out in situ by directing the laser radiation into the exhalation from a patient. Alternatively the exhalation is collected and analyzed in a test cell through photoacoustic detection.

In another embodiment, a photoacoustical detection system and method is set forth for detecting and determining the concentration of a suspected constituent contained in a non-gaseous sample, the suspected constituent having fingerprint absorption wavelengths of between 1700 and 2500 nm. According to this embodiment, vapor is liberated from the non-gaseous sample, such as soil or liquid, using a photoablation process. Toward this end, a $CO_2$ or diode laser may be directed at the sample to photoablate the vapor sample. The liberated vapor sample is thereafter subjected to the photoacoustical detection system and method as hereinabove set forth. The presence of constituents having fingerprint absorption wavelengths between 1700 and 2500 nm are detected by so tuning the $Co:MgF_2$ laser across the wavelengths corresponding to the fingerprint wavelengths of the constituent sought to be detected, detecting the resultant acoustical emissions and processing the detected acoustical signals.

As can be appreciated, a simple, inexpensive and easy to use photoacoustical detection system and method are set forth for detecting the presence of any constituent in a sample having an absorption wavelength of between 1700 and 2500 nm. Certain isotopes, chemicals and compounds having absorption wavelengths within this range which have heretofore required mass spectrographic and/or gas chromatographic analysis can now be analyzed through photoacoustic detection.

Further, as a specific application, metabolic conditions of an organism can be examined through the introduction of stable isotopes and the photoacoustic detection of their exhalation, thereby avoiding the use of other expensive techniques or the use of dangerous radioactive isotopes.

In applications where the sample is not in a desired form, e.g. a form of $CO_2$, a gas chromatograph and combuster can be used to isolate the desired compound and convert it into $CO_2$.

Further, the detection system and method according to the present is adapted for in situ detection of chemicals and compounds having a characteristic fingerprint absorption wavelengths falling within the range of about 1700 to 2500 nm. This would include the detection of certain explosive, chemical warfare materials, rocket exhausts, toxic chemicals, nuclear waste or pollutants heretofore unavailable for photoacoustic detection.

BRIEF DESCRIPTION OF THE DRAWINGS

These and other features and advantages will become appreciated as the same becomes better understood with reference to the specification, claims and drawings wherein:

DESCRIPTION

Figure 1:
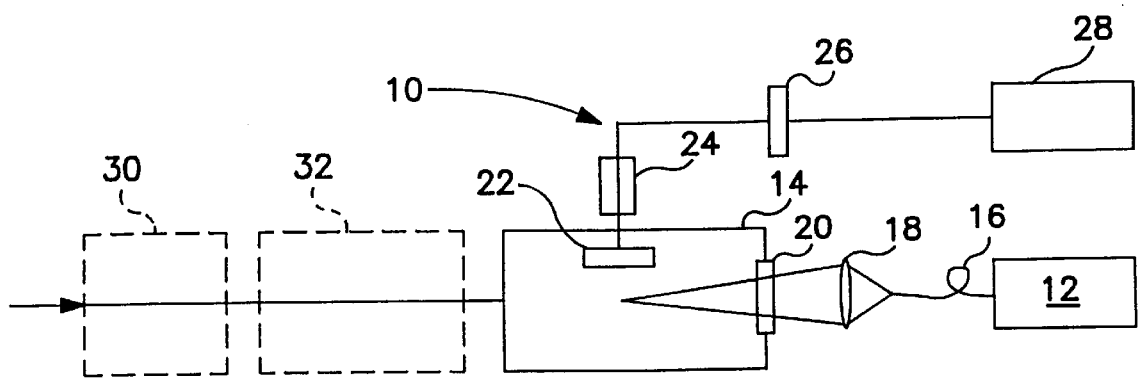
FIG. 1 is a schematic illustration of a detection system and method for isotope ratio analysis according to the present invention.

Referring to FIG. 1, the general aspects of the present invention will now be described. As shown, the present invention is directed to a system 10 for photoacoustical analysis of a sample for a suspected constituent, that constituent having molecules with one or more telltale or fingerprint absorption wavelengths falling in the range of 1700 to 2500 nm, i.e., wave numbers of between 4,000 to 5,880 $cm^{-1}$. For this purpose system 10 includes a source of electromagnetic radiation tunable to wavelengths falling within the aforesaid ranges embodied as a laser 12. Laser 12 is preferably a pulsed, such as a Co:Mg $F_2$ laser, optical parametric oscillator (OPO) laser or diode laser and tunable in the range of 1700 to 2500 nm and having an energy output of at least between 1 to 160 mJ. A Co:Mg $F_2$ laser is preferred in that it has a broad tuning range, can be used for excitation of molecular absorption in their overtone and combination bands in the near infrared region, has a relatively narrow spectral line width of approximately 0.6 $cm^{-1}$ to permit selective excitation of its specific chemical molecules with minimal interference by other molecules, and has sufficient energy output to induce relatively strong acoustical emissions upon excitation.

To direct the output of laser 12 to a test cell 14, the system 10 includes a light transmitter such as an optical fiber 16. The optical fiber 16 communicates the pulsed output of the laser 12 to the test cell 14. The optical fiber 16 can be silicon-dioxide based or fluorine-glass based fibers that have low absorption in the output wavelengths of the laser 12. A lens 18 is adapted to focus the electromagnetic radiation from the fiber 16 into the test cell 14 and the sample contained therein.

The test cell 14 is closed and is charged with a sample containing the suspected constituent by any suitable means. A transparent window 20 provides for the focusing of the output of laser 12 into the test cell 14 to excite selected molecules therein. Alternatively the optical fiber 16 can be positioned to pass into the test cell 14 and to locate the lens 18 within the test cell.

With continued reference to FIG. 1, to detect the acoustical response in the test cell 14, the system 10 includes a sound detector such as a microphone 22 adapted to detect the acoustical response to the excitation of the molecules through the tuning range of the laser 12. The microphone 22 can be any suitable detector for acoustic emissions. In response to a detectable acoustic emission, the microphone 22 generates an electronic signal which is amplified by a pre-amplifier 24 and is thereafter passed through an electrical filter 26. From the filter 26 the signal in response to the detection of the acoustic signal is directed to a data processor 28 which can be remotely located.

As can be appreciated, when the test cell 14 has received the sample containing a gas having a suspected constituent with one or more fingerprint absorption wavelengths falling in the range of 1700 to 2500 nm, the system 10 can be employed to detect the presence of the constituent. Laser 12 is energized to generate pulsed, collimated electromagnetic radiation and is tuned through the range of the suspected fingerprint wavelengths of the constituent. The laser 12 has an output of sufficient energy to create substantial, detectable acoustical signals which are detected by the microphone 22 and processed to obtain data indicating the presence or absence the suspected constituents.

With continued reference to FIG. 1, if the sample to be introduced into the test cell 14 is not in a $CO_2$ form, a gas chromatograph 30 can be used to isolate various components in the sample, the effluents from the gas chromatograph 30 being fed to a combuster 32 to convert the carbon isotope containing components into a $CO_2$ form, for example $^{13}C$, into $^{13}CO_2$.

The isotope containing components now converted to a $CO_2$ form are then provided to the test cell 14 for analysis. As can be appreciated, therefore, the system 10 including the gas chromatograph 30 and combuster 32 can be used to analyze a sample for a carbon isotope Turning to FIG. 2, a further embodiment of the system 10 according to the present invention is shown. This embodiment is adapted to analyze samples in situ in an open air environment for constituent molecules having fingerprint absorption wavelengths falling in the range of 1700 to 2500 nm. For example, an air sample may be analyzed by the system 10 of FIG. 2 for various forms or isotope compositions of CO, $NH_3$, $H_2O$, HCO, $H_2S$, HF, $CH_4$, $C_2H_2$ or $C_2H_6$ or any other composition having molecules with fingerprint absorption wavelengths between 1700 and 2500 nm. System 10 according to FIG. 2 includes the laser 12, optical fiber 16 and lens 18. The lens 18 directs the pulsed, collimated electromagnetic radiation into the vicinity proximate the microphone 22 which is disposed in the open environment to be tested. The open sample proximate the microphone 22 and more particularly the molecules of any constituents having absorption wavelengths of between 1700 to 2500 nm when energized by the laser 12 in the appropriate band width generate acoustical signals detected by the microphone 22. The microphone 22, as described above, generates electrical signals in proportion to the intensity of the acoustical response, those signals being sent to a pre-amplifier 24, through a filter 26 and to a processor 28.

Figure 2:
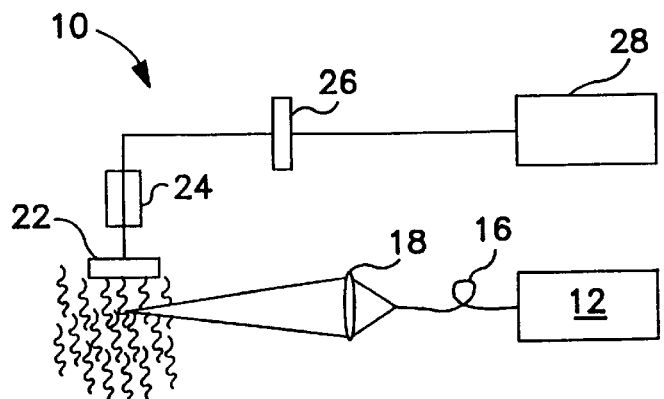
FIG. 2 is a schematic illustration of a photoacoustic detection system and method according to the present invention for the detection of the presence of a constituent in a vapor sample.

The system 10 according to the embodiment shown in FIG. 2 has been used experimentally to detect the spectrum of $CO_2$ containing naturally occurring isotope having wavenumbers of approximately 4800 to 5150 $cm^{-1}$. The laser 12 was a Cobra 2000 Co:MgF$^2$ laser manufactured by Schwartz Electro-Optics, Inc. of Oriand, Fla., the microphone 22 a type 4136 microphone supplied by B&K Instruments, Inc. of Decatur, Ga., the preamplifier 24 was a type 2618 by B&K Instruments, Inc., and the data processor 28 was a Hewlett-Packard 24 was a type 2618 by B&K Instruments, Inc., and the data processor 28 was a Hewlett-Packard 5411 D digitizing oscilloscope. The $CO_2$ gas was released into open air and the output of the laser 12 was focused by the lens 18 to a focal point approximately 3 cm from the microphone 22 located in the released $CO_2$ gas.

Figure 4:
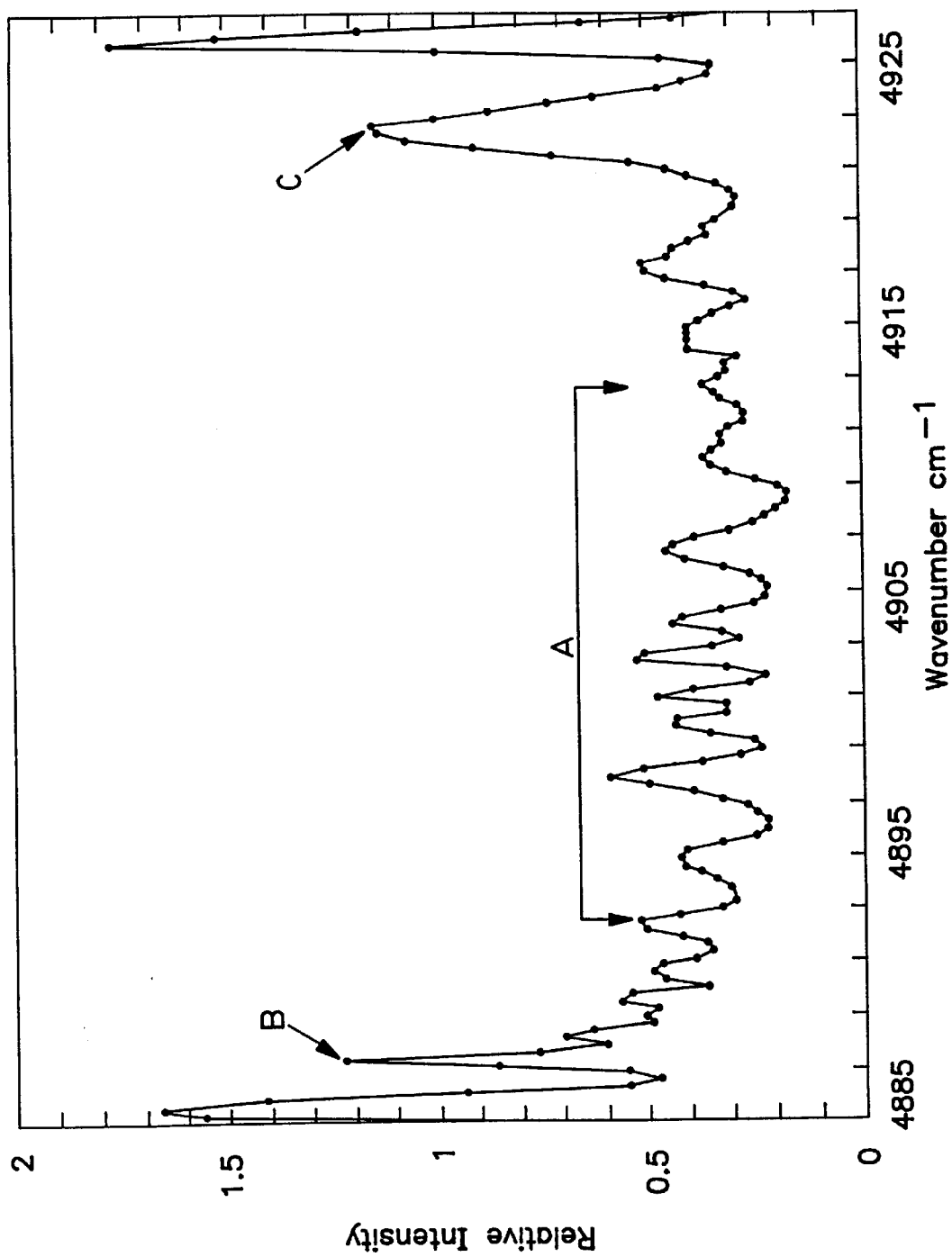
FIG. 4 illustrates a photoacoustic spectrum of $CO_2$ (containing naturally abundant isotopes) from 4885 to 4927 $cm^{-1}$.
Figure 5:
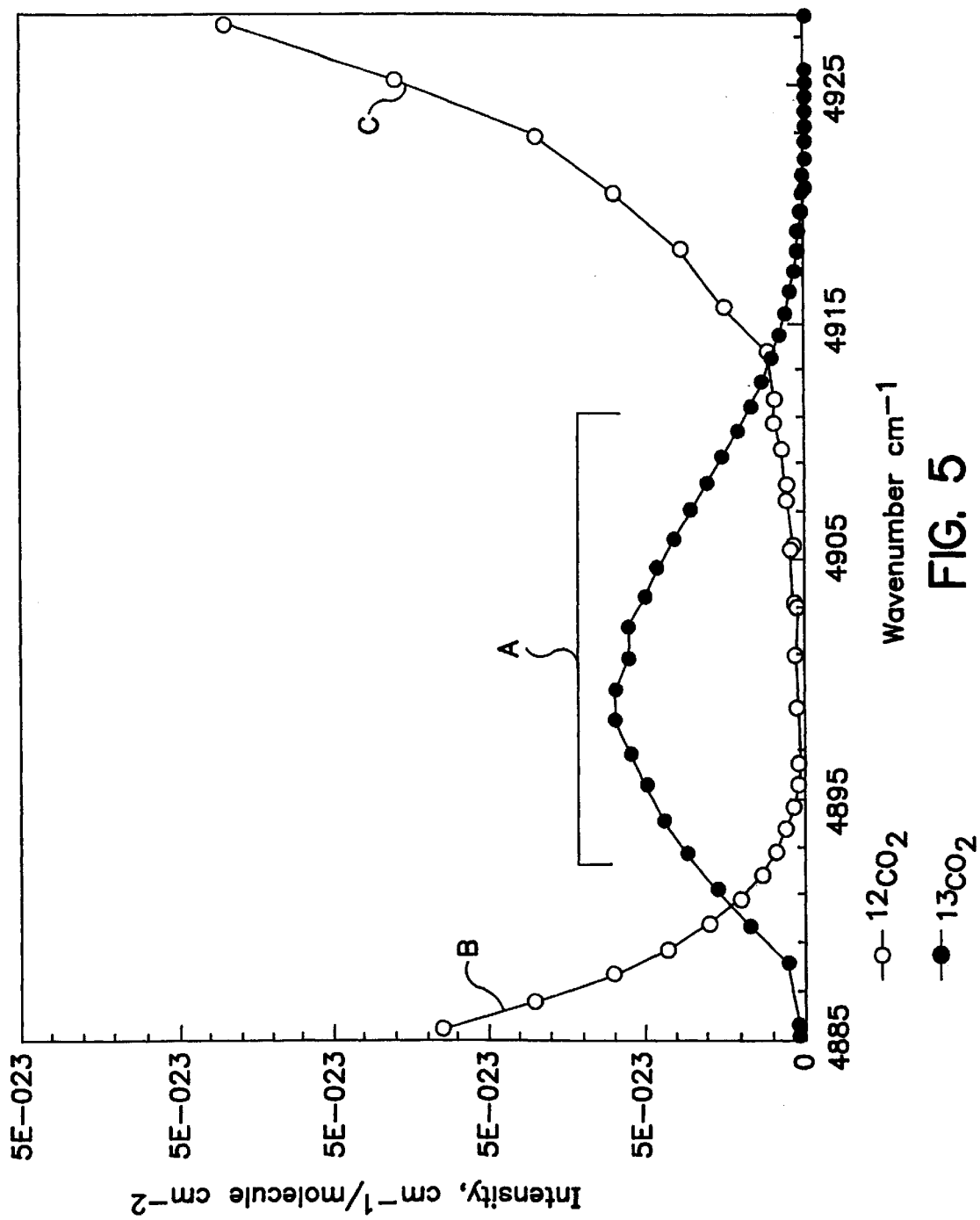
FIG. 5 illustrates the theoretical linestrengths of $^{12}CO_2$ and $^{13}CO_2$ absorption lines at the respective natural abundant composition.

With reference to FIG. 4, there is illustrated the photoacoustically detected spectrum of $CO_2$ using the equipment above containing naturally abundant isotopes from wavenumbers of approximately 4885 to 4927 $cm^{-1}$. As the laser 12 is tuned through the aforesaid range, several spectral structures are detected. $CO_2$ at these structures absorbs energy at the wavenumbers corresponding to the structures, exciting the molecules of $CO_2$ which in turn collide with surrounding molecules creating a detectable acoustical signal. The detectable acoustical response to the introduction of energy across the wavenumbers illustrated signifies in particular the presence of the isotopes most abundant in $CO_2$. With reference to FIG. 5, the theoretical line strength of $CO_2$ containing naturally abundant isotopes in the same range is illustrated. As can be appreciated, the acoustical response measured and illustrated in FIG. 4 closely matches the combined theoretical line strengths for $^{12}CO_2$ and $^{13}CO_2$ illustrated in FIG. 5.

The structures of segment "A" illustrated in FIG. 4 which are attributable to $^{13}CO_2$ whereas the spectral structures "B" and "C" to either side of band "A" are attributable to $^{12}CO_2$. Accordingly, the photoacoustical system 10 of the present invention can be used to resolve a $^{13}CO_2$:$^{12}CO_2$ ratio at natural abundance levels. It is believed that the photoacoustical system 10 according to the present invention can resolve the $^{13}CO_2$:$^{12}CO_2$ isotope ratio at a level as low as $5\times10^{-5}$.

As can be appreciated, the system 10 is relatively simple, inexpensive, easy to use and able to detect trace amounts of suspected constituents in the sample.

With reference to FIG. 1 the system 10 is adapted to be used in methods to examine metabolic rates in organisms such as humans. As but one example, the method includes introducing a stable isotope compound to the organism for uptake and processing by the metabolic system under consideration. The compound may be $^{13}CO$-labeled fat to examine how fat is metabolieed, $^{13}CO$-labeled bile acid and galactose where there is suspected ileal or liver disfunction or $^{13}C$-labeled xylose may be administered to examine small intestine bacterial overgrowth. Where $^{13}C$-labeled fat is administered, the fat is metabolized and the $^{13}C$ isotope is converted to $^{13}CO_2$ and liberated from the body as exhalation. The breath $CO_2$ can be measured in situ in the open environment as illustrated in FIG. 2. Alternatively, samples of the exhaled breath containing the $^{13}CO_2$ are collected in test cells at intervals in measured volumes for photoacoustic detection.

The samples of exhaled air are thereafter analyzed by the system 10. Specifically each or several samples are placed in the test cell 14 and the laser 12 is operated and tuned through the wavelengths from about 4892 to 4913 cm$^{-1}$ for purposes of generating acoustical responses indicative of the presence of $^{13}CO_2$. Power levels are selected to generate detectible acoustical responses as the $^{13}CO_2$ molecules are excited. In this fashion, metabolisms, i.e., the metabolism of fat, can be examined using a stable isotope labeled compound and the system 10. The foregoing method does not require the use of radioactive isotopes and provides fast and reliable detection of the presence of the isotope compound enhancing the efficiency of the method.

Alternatively, the breath $CO_2$ can be analyzed by the photoacoustic detection method and device in situ in front of the patients mouth. This arrangement has advantages of yielding the analysis results nearly instantaneously and in reducing the costs associated with collecting and preserving the samples in test cells.

By examining exhaled breath after administration of $^{13}C$-labeled bile acid and galactose ileal and liver dysfunction can be studied and after $^{13}C$-labeled xylose is administered small intestine overgrowth can be examined. Should the stable isotope compound liberated from the subject not be in a $CO_2$ form the gas chromatograph 30 and combuster 32 can be employed to convert the liberated sample into a $CO_2$ form for analysis by the system 10.

Figure 6:
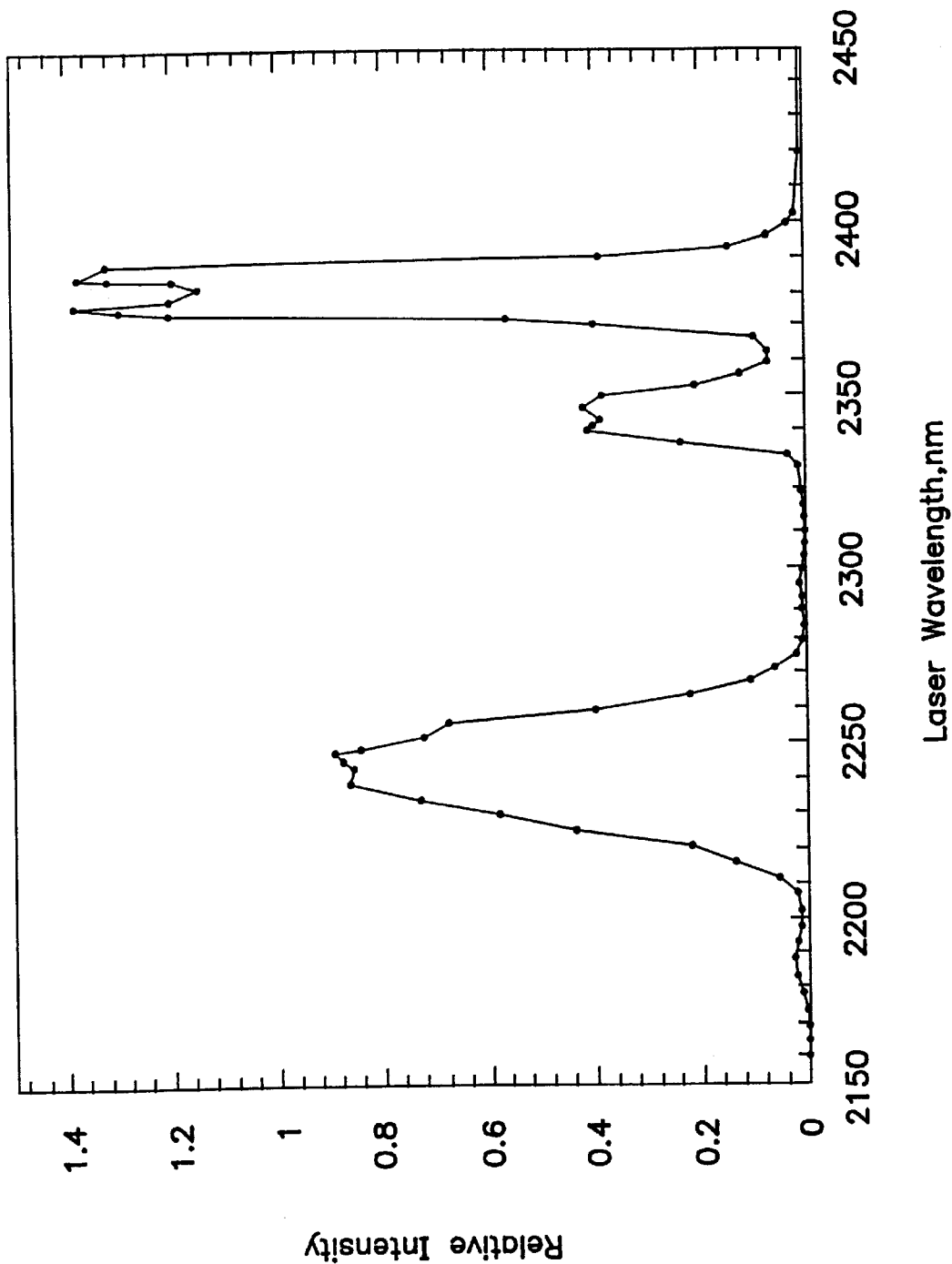
FIG. 6 illustrates a photoacoustic spectrum of methylene chloride vapor in air.

With reference to FIG. 6, there is illustrated the photoacoustically detected spectrum of methylene chloride vapor from approximately 2150 to 2450 nm. The vapor was prepared by bubbling nitrogen gas through methylene chloride liquid, and discharging the entrained vapor into the air.

As the laser 12 is focused into the vapor and tuned through the aforesaid range, several spectral structures are detected. These spectral structures match well with absorption spectrum of methylene vapor known in the literature. These structures can be used as a diagnostic characteristic for analysis of the vapor by the described photoacoustic detection method.

As can be appreciated, the system 10 according to FIG. 2, provides for simple, inexpensive and accurate testing of several gases and vapors in situ. It is believed that concentrations of approximately $1\times10^{-5}$, $6\times10^{-5}$ and $1\times10^{-5}$ for $CH_4$, $C_2H_2$ and $C_2H_6$, respectively, in open air systems can be detected.

Figure 3:
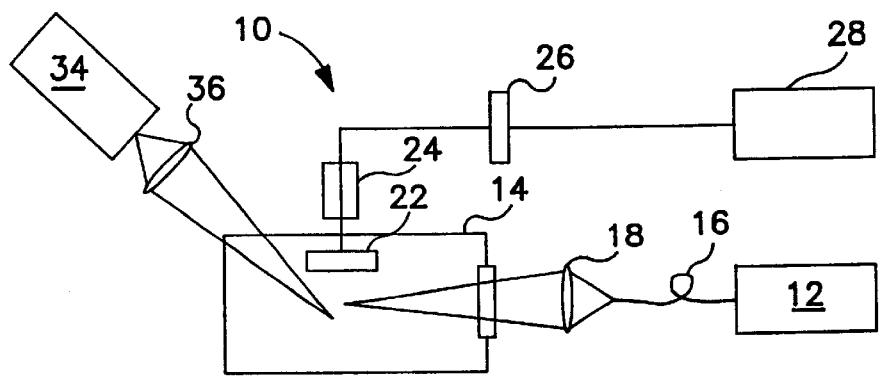
FIG. 3 is a schematic illustration of a photoacoustic detection system and method for detecting the presence of a constituent in a non-gaseous sample.

With reference to FIG. 3, a further embodiment of the system 10 according to the present invention is illustrated. As described above, the system 10 of FIG. 3 includes a laser 12 of the type described above, the output of which is directed through optical fiber 16 and lens 18 into a test cell 14. Within the test cell 14 there is contained a non-vapor sample such as a solid or liquid sample containing semi-volatiles such as explosives, chemical solvents, chemical warfare compounds or the like. According to this embodiment, a device is provided to liberate vapor from the sample for detection by the system 10. This device is, for example, a $CO_2$ or diode laser 34 focused by a lens 36 into the test cell 14 and on to the sample. The energy from the $CO_2$ laser 34, through photoablation, liberates volatiles from the sample for detection by the system 10. As but a few examples, trichloroethylene, chlorobenzene, 1,1-dichloro-ethane, 1,1-dichloro-ethylene, 1-2-dichloro-ethane, chloroform, carbon tetrachloride, 1,1,2,2-tetrachloral ethane, tetrachloro ethylene, ethylene dibromide, 0-cresol, P-creso, M-creso, phenol and naphthalene, which may tend to sink into the soil and aggregate together as non-aqueous phase layers, can be detected in that the aforesaid chemicals have strong absorption lines falling within the wavelength band described above. Still further, many explosives have strong near infrared absorption, for example, ammonium nitrate (at approximately 2300 nm), ammonium perchlorate (at approximately 2000 nm), nitro-benzine and unsymmetrical dimethyl hydrozene as well have strong absorption in the aforesaid wavelength bands. By analyzing a sample taken proximate these explosives or subsequent to their discharge through this, or prior described embodiments where the sample is a vapor, the system 10 can be used to determine the presence of these compounds.

Photoablation may also be used on non-gaseous, i.e. liquid, solid or a mix, sample in situ according to the system 10 of FIG. 2. In this embodiment photoablation liberates a vapor sample from the liquid or solid and the laser 12 is directed into the vapor for detection as described above.

Still further, the photoacoustical technique can be used to monitor the presence of chemical warfare material in air or soil. Taben(GA) has a strong C=N fundamental stretch at 4255 nm, and a corresponding overtone band should occur near approximately 2128 nm. Similarly Sarin(GB) and Soman(GD) have strong P-$CH_3$ fundamental stretch at 3465 nm and a corresponding overtone band should occur at approximately 1732 nm. The system 10 as depicted in FIG. 3 including the $CO_2$ laser 34 (or diode laser) can be used to enhance the detectability of these chemicals to permit non-contact, in situ, real time monitoring of chemical warfare compounds. Where the sample is a vapor, the system 10 according to FIG. 2 can be used.

As but a few other examples, rocket exhaust and more particularly the HCl component thereof can be detected through the system 10 described above.

While certain embodiments of the present invention have been described, it is to be understood that it is subject to many modifications and changes without departing from the spirit and scope of the claims set forth herein.

What is claimed:

1. The method for photoacoustic detection of a suspected constituent in a mixture of background constituents in a sample, the suspected constituent having at least one absorption wavelength in the range of approximately 1700 to 2500 nm, the method comprising the steps of:

isolating the various constituents of the sample such that effluents are created, converting the effluents from the isolation step to a $CO_2$ form of the sample, directing a source of electromagnetic radiation into the sample in the wavelength range of 1700 to 2500 nm corresponding to at least one absorption wavelength of the suspected constituent sufficient to generate an acoustical wave, detecting the acoustic wave, producing an electrical signal proportional to the acoustic wave emissions, and extracting the suspected constituent acoustic emission from the background constituent acoustical emissions.

2. The method of claim 1 including the step of directing a pulsed energy output in the range of 1 to 160 mJ sufficient to generate the acoustical wave.

3. The method of claim 1 including the step of averaging the acoustic emissions corresponding to the selected constituent.

4. A method for examining a metabolic condition of an organism comprising the steps of:

(a) introducing a stable isotope compound into the organism for uptake by the metabolic system, the compound metabolized and removed from the organism as a sample, said sample containing the stable isotope having an absorption wavelength in the infrared portion of the spectrum;

(b) introducing the sample into a gas chromatograph;

(c) directing the effluents from step (b) to a combustor to convert the stable isotope containing components into a $CO_2$ form;

(d) directing the beam output of a laser source into the sample, said laser being tunable between the range of 1700 nm to 2500 nm corresponding to the absorption wave length range of the sample;

(e) generating acoustical signals as a result of the absorption of the laser beam having an energy output of at least 1 to 160 mJ;

(f) detecting the acoustic waves and generating an electrical signal proportional to the acoustical emissions; and (g) processing the electrical signal to extract constituent gas acoustic emissions over a plurality of pulses to improve the signal to noise ratio.

5. The method as claimed in claim 4 wherein the sample is examined in-situ open air.

6. The method as claimed in claim 4 wherein the laser beam is generated by a $Co:M_gF_2$ laser.

7. The method as claimed in claim 4 wherein the laser beam is generated by an optical parametric oscillator (OPO) laser.

8. The method as claimed in claim 4 wherein the laser beam is generated by a diode laser.

9. The method as claimed in claim 4 wherein the sample is collected in a test cell and examined with the laser beam.

10. The method as claimed in claim 9 including the step of directing the laser beam through a lens into an optical fiber to the sample.

* * * * *